(12) United States Patent
Brodeur et al.

(10) Patent No.: US 6,945,991 B1
(45) Date of Patent: Sep. 20, 2005

(54) COMPOSITE TUBULAR PROSTHESES

(75) Inventors: Christopher Brian Brodeur, Andover, MN (US); Jason Peter Hill, Cottage Grove, MN (US); David John Sogard, Edina, MN (US); Susan M. Shoemaker, Elk River, MN (US)

(73) Assignee: Boston Scientific/SciMed Life Systems, Inc., Maple Grove, MN (US)

( * ) Notice: Subject to any disclaimer, the term of this patent is extended or adjusted under 35 U.S.C. 154(b) by 140 days.

(21) Appl. No.: 09/723,852

(22) Filed: Nov. 28, 2000

(51) Int. Cl.$^7$ ................................................ A61F 2/06
(52) U.S. Cl. ................................................ 623/1.13
(58) Field of Search ............................. 623/1.13, 1.14

(56) References Cited

U.S. PATENT DOCUMENTS

| | | |
|---|---|---|
| 4,925,710 A | 5/1990 | Buck et al. |
| 5,123,917 A | 6/1992 | Lee |
| 5,151,165 A | 9/1992 | Huynh |
| 5,282,824 A | 2/1994 | Gianturco |
| 5,389,106 A | 2/1995 | Tower |
| 5,466,509 A | 11/1995 | Kowligi et al. |
| 5,507,771 A | 4/1996 | Gianturco |
| 5,562,697 A | 10/1996 | Christiansen |
| 5,562,728 A | 10/1996 | Lazarus et al. |
| 5,591,195 A | 1/1997 | Taheri et al. |
| 5,620,763 A | 4/1997 | House et al. |
| 5,628,788 A | 5/1997 | Pinchuk |
| 5,653,697 A | 8/1997 | Quiachon et al. |
| 5,674,241 A | 10/1997 | Bley et al. |
| 5,700,285 A | 12/1997 | Myers et al. |
| 5,713,917 A | 2/1998 | Leonhardt et al. |
| 5,718,973 A | 2/1998 | Lewis et al. |
| 5,723,003 A * | 3/1998 | Winston et al. ................. 623/1 |
| 5,735,892 A | 4/1998 | Myers et al. |
| 5,749,880 A | 5/1998 | Banas et al. |
| 5,810,870 A | 9/1998 | Myers et al. |
| 5,925,074 A | 7/1999 | Gingras et al. |
| 5,925,075 A | 7/1999 | Myers et al. |
| 6,312,458 B1 * | 11/2001 | Golds ......................... 623/1.13 |
| 6,398,803 B1 * | 6/2002 | Layne et al. ................ 623/1.13 |

FOREIGN PATENT DOCUMENTS

| | | | |
|---|---|---|---|
| EP | 0893108 | * | 1/1999 |
| WO | WO 95/05132 | | 2/1995 |
| WO | WO 95/05555 | | 2/1995 |
| WO | WO 96/28115 | | 9/1996 |
| WO | WO 98/00090 | | 1/1998 |
| WO | WO 00/45741 | | 8/2000 |
| WO | WO 00/45743 | | 8/2000 |
| WO | WO 00/71057 A1 | | 11/2000 |
| WO | WO 01/01887 A1 | | 1/2001 |

* cited by examiner

*Primary Examiner*—Michael Thaler
(74) *Attorney, Agent, or Firm*—Hoffmann & Baron, LLP

(57) ABSTRACT

A tubular implantable prosthesis is formed of porous expanded polytetrafluoroethylene. The tubular prosthesis includes a substantially continuous ePTFE tubular first body and perimetrically non-continuous second tubular body. A circumferentially deformable support structure is interposed between the inner and outer tubular bodies. The second tubular body is formed of a plurality of elongate PTFE strips. The strips are secured to the first body and arranged longitudinally in a non-overlapping relationship. The prosthesis provides for both axial and radial compliance.

9 Claims, 2 Drawing Sheets

8

9

10

11

12

13

COMPOSITE TUBULAR PROSTHESES

FIELD OF INVENTION

The present invention relates generally to a tubular implantable prosthesis formed of porous expanded polytetrafluoroethylene. More particularly, the present invention relates to a composite, multi-layered endoprosthesis having increased axial and circumferential compliance.

BACKGROUND OF RELATED TECHNOLOGY

An intraluminal prosthesis is a medical device used in the treatment of diseased blood vessels. An intraluminal prosthesis is typically used to repair, replace, or otherwise correct a diseased or damaged blood vessel. An artery or vein may be diseased in a variety of different ways. The prosthesis may therefore be used to prevent or treat a wide variety of defects such as stenosis of the vessel, thrombosis, occlusion, or an aneurysm.

One type of intraluminal prosthesis used in the repair of diseases in various body vessels is a stent. A stent is a generally longitudinal tubular device formed of biocompatible material which is useful to open and support various lumens in the body. For example, stents may be used in the vascular system, urogenital tract and bile duct, as well as in a variety of other applications in the body. Endovascular stents have become widely used for the treatment of stenosis, strictures, and aneurysms in various blood vessels. These devices are implanted within the vessel to open and/or reinforce collapsing or partially occluded sections of the vessel.

Stents are generally open-ended and are radially expandable between a generally unexpanded insertion diameter and an expanded implantation diameter which is greater than the unexpanded insertion diameter. Stents are often flexible in configuration, which allows them to be inserted through and conform to tortuous pathways in the blood vessel. The stent is generally inserted in a radially compressed state and expanded either through a self-expanding mechanism, or through the use of balloon catheters.

A graft is another commonly known type of intraluminal prosthesis which is used to repair and replace various body vessels. A graft provides a lumen through which blood may flow. Grafts are typically tubular devices which may be formed of a variety of materials, including textiles, and non-textile materials. One type of particularly useful non-textile material for an implantable intraluminal prosthesis is polytetrafluoroethylene (PTFE). PTFE exhibits superior biocompatibility and low thrombogenicity, which makes it particularly useful as vascular graft material in the repair or replacement of blood vessels. In vascular applications, grafts are often manufactured from expanded polytetrafluoroethylene (ePTFE) tubes. These tubes have a microporous structure which allows natural tissue ingrowth and cell endothelization once implanted in the vascular system. This contributes to long term healing and patency of the graft.

Grafts formed of ePTFE have a fibrous state which is defined by interspaced nodes interconnected by elongated fibrils. The spaces between the node surfaces that is spanned by the fibrils is defined as the internodal distance (IND). Porosity of a graft is generally described using IND. In order to have proper tissue ingrowth and cell endothelization, grafts must have sufficient porosity obtained through expansion. When the term expanded is used to describe PTFE, it is intended to describe PTFE which has been stretched, in accordance with techniques which increase the IND and concomitantly porosity. The stretching may be uni-axial, bi-axial, or multi-axial. The space between the nodes is occupied by the stretched fibrils.

Properties such as tensile strength, tear strength and circumferential (hoop) strength are all dependent on the expansion process. Expanding the film by stretching it in two directions that are substantially perpendicular to each other, for example longitudinally and transversely, creates a biaxially oriented material. Films having multi-axially-oriented fibrils may also be made by expanding the film in more than two directions. Porous ePTFE grafts have their greatest strength in directions parallel to the orientation of their fibrils.

Longitudinal compliance is of particular importance to an intraluminal prosthesis that is delivered through tortuous pathways of a blood vessel to the implantation site where it is expanded. Conventional PTFE containing grafts exhibit low longitudinal compliance and as such have decreased flexibility, which makes intraluminal delivery more difficult. Additionally, conventional PTFE containing grafts may fail at the outer circumference when the PTFE is at a stretch limit such as at a bend point around a corner.

Accordingly, it is desirable to provide a PTFE graft that has high axial and longitudinal compliance. Additionally, it is desirable to provide a PTFE that has a low failure rate at points where the PTFE outer circumferential is at a stretch limit.

SUMMARY OF THE INVENTION

The present invention is directed towards an implantable composite tubular prosthesis. The composite has three layers; a first tubular ePTFE body, a second perimetrically non-continuous tubular body, and a circumferentially support structure between the tubular bodies. The first tubular body may be the inner tubular body and the second tubular body may be the outer tubular body. Alternatively, the first tubular body may be the outer tubular body and the second tubular body may be the inner tubular body. The outer layer may be ePTFE or PTFE.

More particularly, the present invention provides a composite implantable tubular prosthesis which has a first substantially continuous ePTFE tubular body and a second tubular body. A circumferentially deformable support structure is interposed between the two tubular PTFE bodies. The second tubular body is formed of a plurality of elongate PTFE strips. The strips are arranged longitudinally in a non-over-lapping relationship and secured to the first body desirably through and about the distensible support structure. Use of the non-overlapping strips of the second tubular body provide axial and circumferential compliance to the prosthesis. In an alternative embodiment, the inner tubular body may be formed of non-overlapping ePTFE strips, overlapping the discontinuities in the outer tubular body.

The present invention also provides an implantable composite intraluminal prosthesis having a first perimetrically non-continuous polytetrafluoroethylene tubular inner body; a second perimetrically non-continuous outer tubular body; and a circumferentially deformable support structure interposed between the inner and outer tubular bodies. Both the outer tubular body and the inner tubular body are formed of polytetrafluoroethylene strips, having a longitudinal length greater than its width, and the strips within each tubular body arranged in non-over-lapping relationship, with the strips of the inner tubular body overlapping the discontinuities of the outer tubular body, and secured in the overlap, whereby axial and circumferential compliance is provided to the prosthesis.

Another embodiment of the present invention provides for a method of providing axial and circumferential compliance to an intraluminal prosthesis stent/graft composite including providing a substantially continuous polytetrafluoroethylene tubular first body; positioning a deformable support structure over the tubular first body; positioning PTFE strip components in non-overlapping relationship, lengthwise along the length of the first body and support structure to form a tubularly shaped second body; and attaching the strips of the second body to the first body.

A further embodiment of the present invention provides for a method of providing axial and circumferential compliance to an intraluminal prosthesis stent/graft composite including positioning PTFE strip components, having a length greater than their width, lengthwise along a mandrel, in non-overlapping relationship, to form a circumferentially non-continuous polytetrafluoroethylene tubular first body; positioning a deformable support structure over the first body; positioning PTFE strip components, lengthwise along the longitudinal axis of the first body, in non-overlapping relationship but overlapping the discontinuities of the first body to form a second body; and securing the second body to the first body to form the prosthesis.

DETAILED DESCRIPTION OF THE INVENTION

Figure 1:
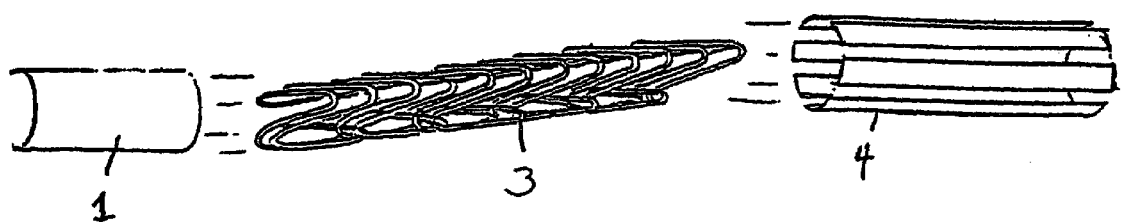
FIG. 1 is an exploded perspective view showing an implantable composite tubular prosthesis according to the present invention, illustrating first body 1, support structure 3, and second body 4.
Figure 1:
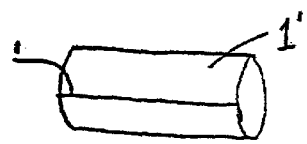

The prosthesis of one desired embodiment of the present invention is a composite implantable intraluminal prosthesis which is particularly suited for use as a vascular graft. As shown in FIG. 1, this composite prosthesis includes a multi-layer graft structure with a circumferentially deformable support structure 3 interposed between an ePTFE first tubular body 1, and non-continuous second body 4, formed of PTFE components. The present description is meant to describe all the desired embodiments, and is not meant to limit the invention in any way.

As shown in FIG. 1, first body 1 may be a substantially continuous tubular structure, formed by various methods such as by forming a tube with a sheet, a spirally wrapped strip or extruding a tube. For example, if a sheet is used, the first body 1 can be formed by wrapping the sheet around a longitudinal axis, such as around a mandrel (not shown), to form a tubular body 1' with a longitudinal seam 2'. Continuous, as used herein, refers to a tubular structure whose surface extends substantially uninterrupted throughout the longitudinal length thereof. In the case of an extruded tube, the tubular structure is completely uninterrupted. A substantially uninterrupted tubular structure exhibits enhanced strength and sealing properties when used as a vascular graft. Furthermore, the first tubular body may consist of one single layer or it may consist of multiple layers of the PTFE sheet around the longitudinal axial to create a multi-layer inner tube. The first body may be the inside tubular body and the second body may be the outer tubular body. Alternatively, the first body may be the outer tubular body and the second body may be the inner tubular body.

Figure 2:
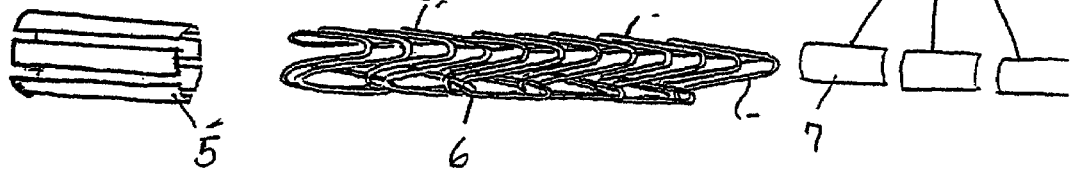
FIGS. 2–4 are exploded perspective views of alternative structures of the prosthesis.

As shown in FIG. 2, first tubular body 5 may be formed of longitudinal strips or components. Alternatively, the first tubular body may be formed of one or more helically wound strips or components 8 and 11 as shown in FIGS. 3 and 4.

Figure 3:
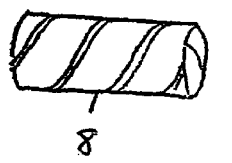
Figure 3:
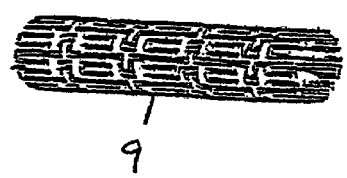
Figure 3:
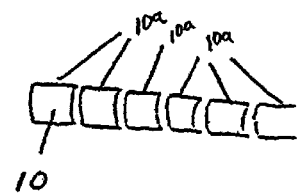
Figure 4:
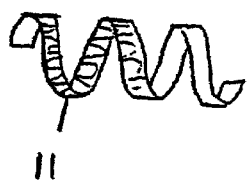
Figure 4:
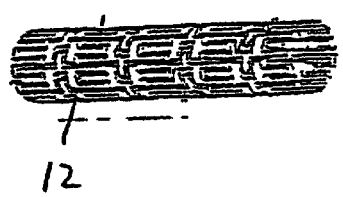
Figure 4:
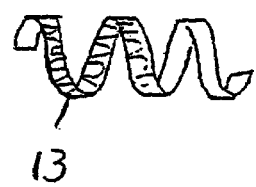

As shown herein, the second tubular body shown in FIGS. 1–4 form perimetrically non-continuous bodies from PTFE components tubularly assembled. Non-continuous, as used herein, refers to a tubular structure which is not substantially uninterrupted along its length. The non-continuous structure of the outer tubular body provides the composite prosthesis with enhanced radial and axial compliance. The radial and axial compliance can, in fact, be varied with the different outer PTFE bodies which may be used, as may be suitable particularly for the use of the intraluminal prosthesis. Perimetrically, as used herein, refers to the tubular structure being non-continuous either around the circumference of the tubular member (i.e. as shown as element 4 of FIG. 1) or along the longitudinal axis of the tubular member (i.e. as shown as element 7 in FIG. 2). The non-continuous second body 4 is formed of PTFE components which may be, for example, coated, extruded, woven or braided. As seen in FIGS. 2 and 3, the second body 7 and 10 may be individual strips or longitudinally arranged segments 7a and 10a which may be non-continuous.

In a desired embodiment, the PTFE components forming the second tubular body are expanded PTFE (ePTFE) strips. Generally ePTFE strips are stretched in the longitudinal direction of the strip. When two or more components are combined to form the outer tubular body, the resultant tubular body possesses a biaxial, or multi-axial resultant orientation in the aggregate. Because ePTFE exhibits increased strength in the direction of its stretching, the ePTFE tubularly assembled prosthesis exhibits the advantage of the increased strength of a biaxial or multi-axial stretched film, but also exhibits longitudinal compliance because of the presence of a non-continuous tubular surface.

When both tubular bodies are formed of perimetrically non-continuous strips, as in FIG. 2, the two bodies desirably have radially overlapping portions which may be adhered to one another to form the composite prosthesis. As shown in FIG. 4, continuous longitudinal strips 11 and 13 may be sinusoidal, extending in a wave pattern down the length of the tubular bodies.

The first tubular layer may be bonded to the second tubular layer through spaces in the open wall of the stent. The bonding may be effectuated with the use of an adhesive, or by adhering the layers together without an adhesive. Bonding of the PTFE layers without an adhesive may take place by such methods as thermally bonding, also known as laminating. Furthermore, the stent may be adhered to the first tubular layer, the second tubular layer, or both. Similarly, such adherence may take place with or without the use of an adhesive. The components may be fully or partially bonded.

The present invention also contemplates that a deformable support member or stent is used with the prosthesis of the present invention to provide a composite intraluminal prosthesis. A deformable support member is desirably a stent which is positioned between the first and second tubular bodies. Stent 3 and 6 is a length of wire distensible material that has longitudinally adjacent waves being nested along the length of the tubular body, as shown in FIGS. 1 and 2. Overlying the deformable support member is perimetrically non-continuous second body 4, having longitudinally arranged strips.

Various stent types and stent constructions may be employed in the invention. Useful stents include, without limitation, self-expanding stents and balloon expandable stents. The stents may be capable of radially contracting, as well, and in this sense can be best described as radially or circumferentially distensible or deformable. Self-expanding stents include those that have a spring-like action which causes the stent to radially expand, or stents which expand due to the memory properties of the stent material for a particular configuration at a certain temperature. Nitinol is one material which has the ability to perform well while both in spring-like mode, as well as in a memory mode based on temperature. Other materials are of course contemplated, such as stainless steel, platinum, gold, titanium and other biocompatible metals, as well as polymeric stents.

The configuration of the stent may be of any geometry. As shown in FIGS. 1 and 2, useful wire stents 3 and 6 include longitudinally adjacent waves being nested along the length of the tubular body with the peaks of the longitudinally nested waves linearly aligned. The deformable support structure may include a plurality of spaced apart circumferentially extending bands. Tubular stents 9 and 12, useful in the present invention, also include those formed by etching or cutting a pattern from a tube as shown in FIGS. 3 and 4. Such stents are often referred to as slotted stents. Furthermore, stents may be formed by etching a pattern into a material or mold and depositing stent material in the pattern, such as by chemical vapor deposition or the like.

PTFE components that can be used for the tubular bodies may be selected from the group consisting of yarns, fibers, sheets and tubes. The tubular bodies of the present invention may be wrapped by various methods. Useful wrap methods include a segmented tube, segmented helical, helical, longitudinal strip, segmented longitudinal helical and combinations thereof.

Sealants that may be used in the prosthesis include fluorinated ethylene propylene (FEP), polyurethane, and silicone. Additional sealants include biological materials such as collagen, and hydrogels, polymethylmethacrylate, polyamide, and polyurethane-polycarbonate. Elastomers as sealants will have less impact on flexibility. A suitable sealant provides a substantially sealed outer tube without significantly reducing longitudinal and axial compliance.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

What is claimed is:

1. An implantable composite tubular prosthesis comprising:
   a first plurality of generally straight polytetrafluoroethylene strips, said first strips being arranged to define a first tubular form with said first strips being generally parallel and arranged in non-overlapping relationship to create gaps therebetween;
   a second plurality of, separate and independent polytetrafluoroethylene strips said second strips being arranged to define a second tubular form with said second strips being generally parallel and arranged in non-overlapping relationship to create gaps therebetween; and
   a circumferential deformable support structure interposed between said first tubular form and said second tubular form, wherein the strips of said second tubular form at least partially overlap the gaps of said first tubular form to secure the support structure.

2. A method of providing axial and circumferential compliance to an intraluminal prosthesis stent/graft composite comprising:
   a) providing a plurality of generally parallel, separate and independent polytetrafluoroethylene strips arranged to define a first tubular form, said strips being arranged in non-overlapping relationship to form gaps therebetween;
   b) positioning a deformable support structure over said first tubular form;
   c) positioning a second plurality of generally parallel, separate and independent polytetrafluoroethylene strips, said second strips being arranged in non-overlapping relationship to define a second tubular form having gaps between the second strips, wherein said second tubular form is positioned at least partially over the gaps of said first tubular form; and
   d) securing said second tubular form to said first tubular form to form said prosthesis.

3. An implantable composite tubular prosthesis comprising:
   a first plurality of generally straight polytetrafluoroethylene strips, said first strips being arranged to define a first tubular form with said first strips being generally parallel and arranged in non-overlapping relationship to create gaps therebetween;
   a second plurality of coaxial non-continuous polytetrafluoroethylene segments being arranged to define a second tubular form with said segments being arranged along a longitudinal axis of said tubular prosthesis creating gaps between each segment; and
   a circumferential deformable support structure interposed between said first tubular form and said second tubular form, wherein the segments of said second tubular form at least partially overlap the gaps of said first tubular form to secure the support structure.

4. The composite tubular prosthesis according to claim 3, wherein said first tubular form is an inner tubular body and said second tubular form is an outer tubular body of said prosthesis.

5. The composite tubular prosthesis according to claim 3, wherein the PTFE of said first tubular form is expanded PTFE.

6. The composite tubular prosthesis according to claim 3, wherein said deformable support structure is a stent.

7. The composite tubular prosthesis as in claim 3, wherein the PTFE of said second tubular form is ePTFE.

8. The composite tubular prosthesis according to claim 3, wherein the deformable support structure is a wire stent with longitudinally adjacent waves being nested along the length of said first tubular form and peaks of said longitudinally nested waves are linearly aligned.

9. The composite tubular prosthesis according to claim 3, wherein the first tubular form is secured to said second tubular form by thermal bonding.

* * * * *